(12) United States Patent
Chen

(10) Patent No.: US 8,970,837 B2
(45) Date of Patent: Mar. 3, 2015

(54) APPARATUS FOR TAKING AN ACCURATE PHOTOMETRIC MEASUREMENT OF A LIQUID

(71) Applicant: Laxco Inc., Bothell, WA (US)

(72) Inventor: Congliang Chen, Bothell, WA (US)

(*) Notice: Subject to any disclaimer, the term of this patent is extended or adjusted under 35 U.S.C. 154(b) by 25 days.

(21) Appl. No.: 13/830,201

(22) Filed: Mar. 14, 2013

(65) Prior Publication Data

US 2014/0268125 A1 Sep. 18, 2014

(51) Int. Cl.
*G01N 21/03* (2006.01)

(52) U.S. Cl.
CPC ..................... *G01N 21/03* (2013.01)
USPC .............. 356/246; 356/440; 422/102

(58) Field of Classification Search
USPC .......... 356/432–440, 244, 246; 422/554, 425, 422/102–104; 436/164, 178, 177
See application file for complete search history.

(56) References Cited

U.S. PATENT DOCUMENTS

| | | | |
|---|---|---|---|
| 5,472,671 A | 12/1995 | Nilsson et al. | |
| 6,707,556 B2 * | 3/2004 | Turner et al. | 356/436 |
| 6,887,432 B2 | 5/2005 | Kansy et al. | |
| 7,092,084 B2 * | 8/2006 | Payne | 356/246 |
| 7,948,619 B2 | 5/2011 | Huemer | |
| 8,110,160 B2 | 2/2012 | Assmann et al. | |
| 2012/0156796 A1 | 6/2012 | Drechsler et al. | |

* cited by examiner

*Primary Examiner* — Hoa Pham
(74) *Attorney, Agent, or Firm* — Cicero Patent Services, PLLC

(57) ABSTRACT

An apparatus for taking an accurate photometric measurement of a liquid by way of forming a specimen volume of a controlled optical path length for use with photometric measurement equipment is disclosed herein. In some embodiments, the apparatus comprises a transparent body configured for displacing a volume of a fluid and at least one support element wherein the support element is configured to maintain the transparent body at a location such that specimen fluid may enter a void volume to form a specimen volume of a controlled optical path length. In some embodiments, the apparatus comprises a plurality of transparent bodies interconnected by a web such that the transparent bodies are maintained at a spacing arrangement which allows for them to be inserted into the wells of a microplate in order to create a plurality of specimen volumes of a controlled optical path length.

9 Claims, 8 Drawing Sheets

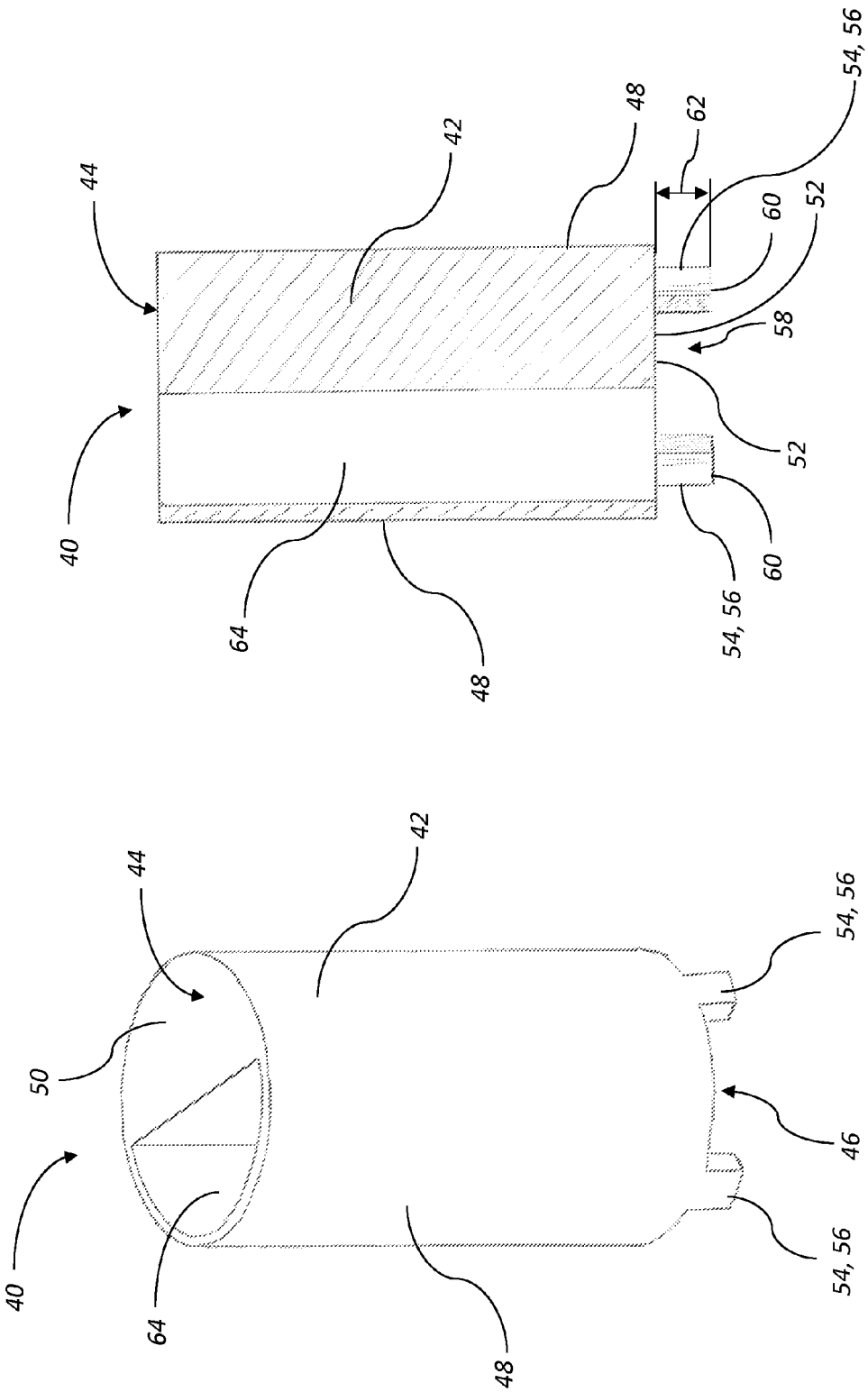

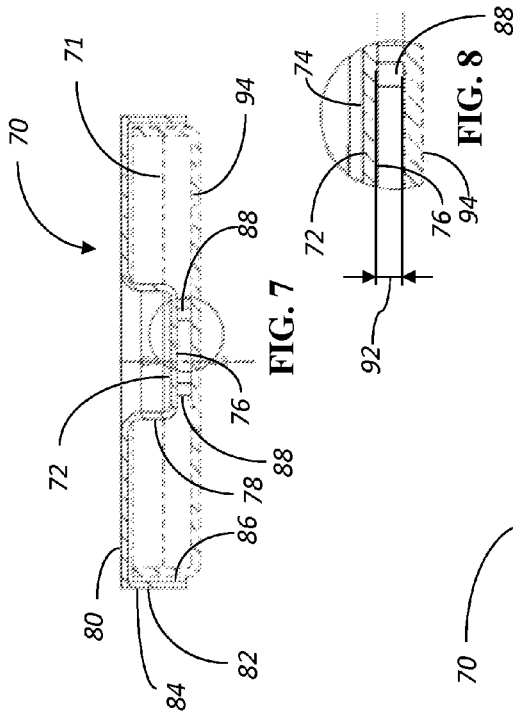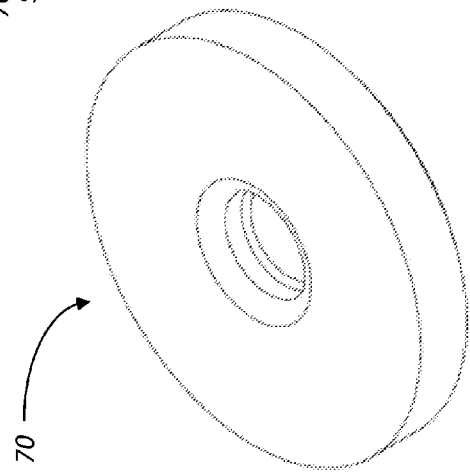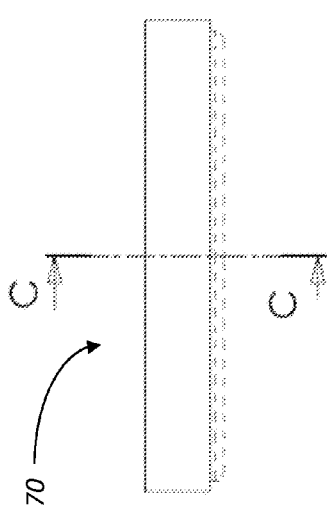

SECTION E-E

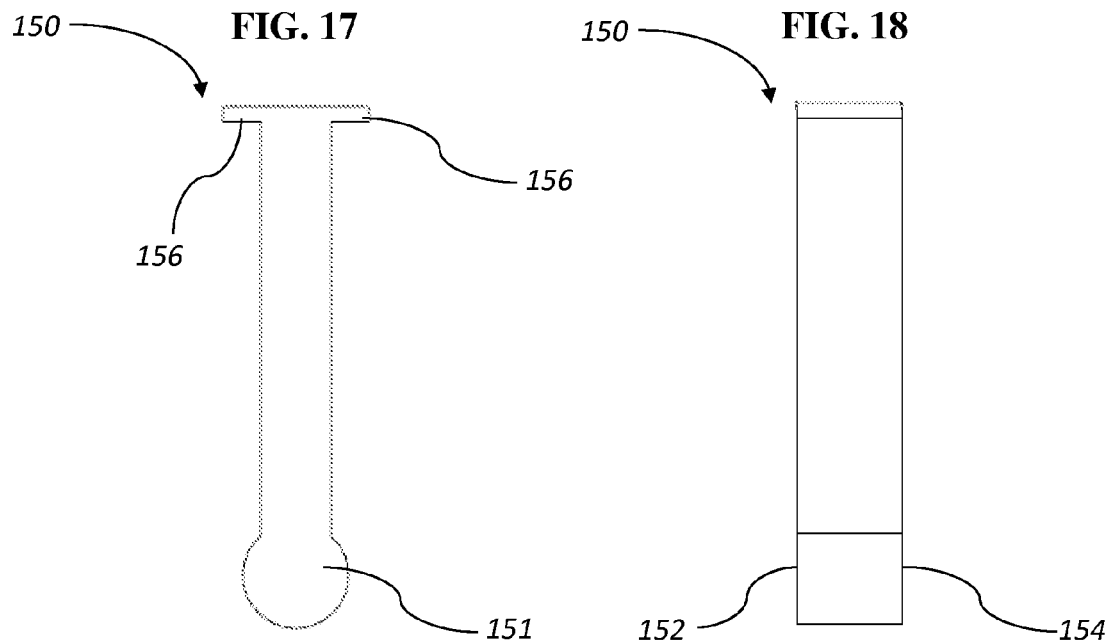
FIG. 17  FIG. 18
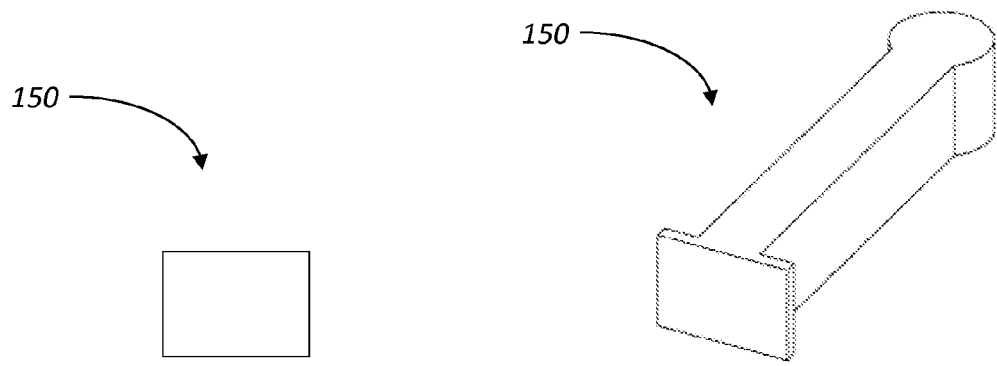
FIG. 19  FIG. 20

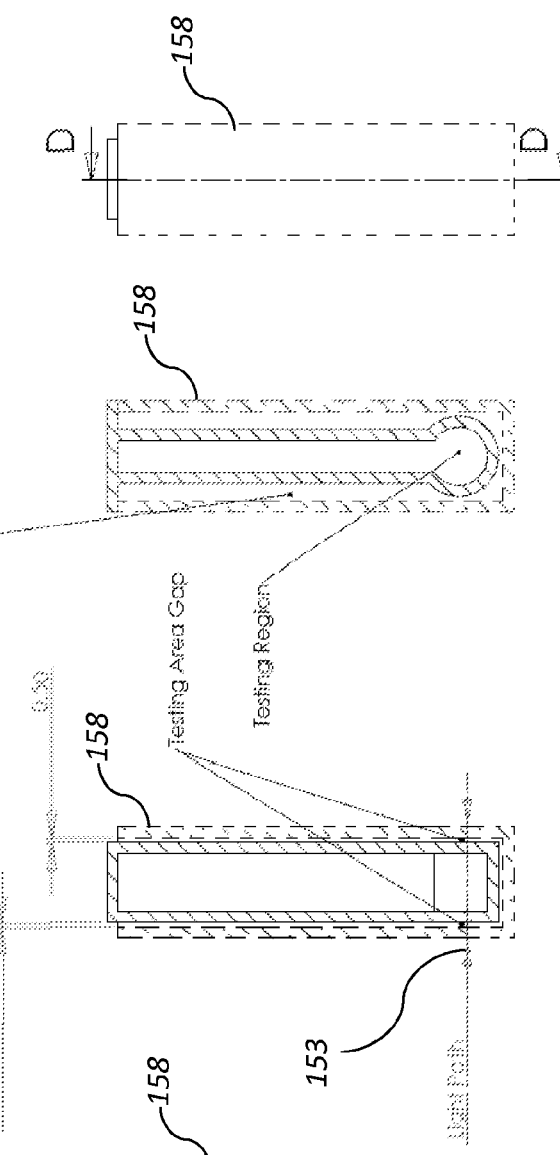
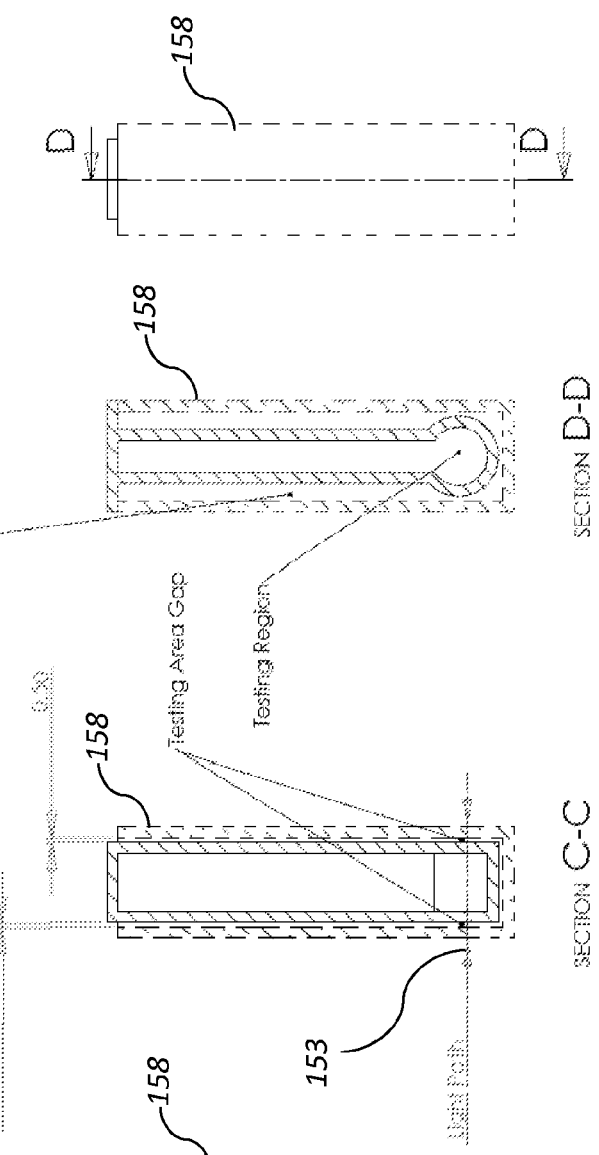
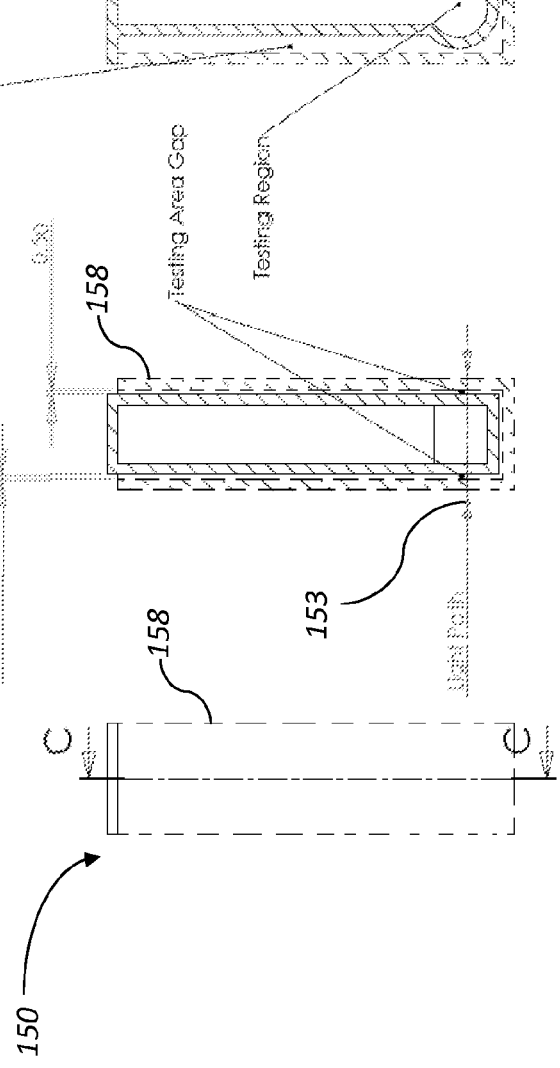
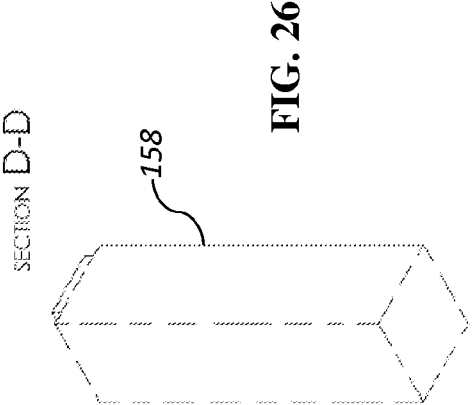
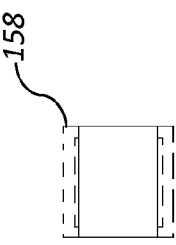
FIG. 21  FIG. 22  FIG. 23  FIG. 24
FIG. 25  FIG. 26

APPARATUS FOR TAKING AN ACCURATE PHOTOMETRIC MEASUREMENT OF A LIQUID

FIELD OF THE DISCLOSURE

The present disclosure relates generally to the field of photometric measurement of liquids in an optical system and, more particularly, an apparatus taking an accurate photometric measurement of a liquid by way of forming a specimen volume of a controlled optical path length for use with photometric measurement equipment.

BACKGROUND

This section provides background information related to the present disclosure which is not necessarily prior art.

There is an ever growing need for apparatuses and methods for taking accurate photometric measurements of liquids at increased throughputs. The pharmaceutical industry, for example, may be required by government agencies to perform tests on hundreds of thousands of drugs specimens prior to receiving approval to market certain drugs. The potential marketability of specific drugs must overcome the substantial barrier of possessing a marketability potential great enough to justify the financial cost of such laborious and time consuming testing. The cost of such testing is not solely born by pharmaceutical companies as at least some of the cost is passed on to consumers. Additionally, there is a great social cost resulting, at least partially, from the high cost of bringing pharmaceuticals to market. Because a high level of market potential is required to justify the research and development of pharmaceuticals, including the cost of testing of said pharmaceuticals as required by government agencies, there is a tendency within the pharmaceutical industry toward researching and developing products which address ailments of the affluent while neglecting to address ailments which disproportionality affect poor populations.

One variable which has a considerable effect on the accuracy of a reading is the ability to control the optical path length of a volume of a specimen fluid. The optical patent length simply refers to the distance that light travels through a specimen fluid prior to being measured once it exits the fluid. Spectrometers, for example, are commonly used to measure the optical properties of light after it has exited a test specimen but the optical properties of the exiting light is a function of the distance through which it travels through a medium, e.g. the specimen fluid. Therefore, controlling the optical path length is of great importance in obtaining accurate photometric measurements of a fluid and, resultantly, certain apparatuses address this issue.

A variety of cuvette designs exist to control the optical path length of a specimen fluid by comprising geometrical constraints over a volume of specimen fluid within the bottom of an inner region of the cuvette. As a result, the controlled optical path length is created when light is projected through one side of the cuvette and is measured on the opposite side of the cuvette. For example, U.S. Pat. Appl. Pub. No. 2012/0156796 A1, with applicants Drechsler et al., a Pub. Date of Jun. 21, 2012, and which is fully incorporated by reference herein, discloses a cuvette for photometric measurement of liquids, wherein the cuvette comprises a lower measurement chamber. The optical path length may be measured horizontally across a portion of the lower measurement chamber and, more specifically, the optical path length may be the distance between a lower front wall and a lower back wall. Some cuvettes exist which comprise two different optical path lengths based on the from which side of the cuvette the beam of light is projected. For example, the Eppendorf UVette® allows for a user to choose between two optical path lengths, e.g. 10 mm and 2 mm, with a single 90° rotation. Cuvette designs such as these examples are also particularly useful when testing requires a very small optical path length, for example a very dark fluid may require a small optical path length because a measurable amount of light might not exit the fluid if the length is too long.

A standard tool analytical research and clinical diagnostic testing laboratories, wherein large numbers of tests must often be run, is a flat plate with a plurality of wells known as a microtitre plate or simply a microplate. It is typical for a microplate to have upward of 1536 sample wells, although larger microplates have been manufactured. Each of the plurality of wells essentially serves as small test tube or cuvette and are commonly filled with volumes of specimen fluid to have photometric measurements taken. The measurements often must be taken by projecting light in the vertical direction, e.g. from above the microplate wells, to have a reading photometric measurement taken from below the microplate. The optical path length is thus dependent on the fill level of each well and so care must be taken to control the optical path length by controlling the volume added to each well. As the size of the wells in decreased in order to produce more wells per microplate this problem becomes exacerbated by the effects of surface tension. Surface tension along the perimeter of a sample well may form a meniscus at the top surface of the specimen fluid which may decrease the accuracy of a photometric measurement.

The various attempts at improving the available apparatuses and methods of taking accurate photometric measurements of liquids suffer any or all of: requiring individual treatment of each specimen, e.g. various cuvettes with lower measurement chambers designed for a horizontal optical path length must be placed one at a time into a spectrometer for photometric measurement; and requiring very tight control over the volume of specimen fluid placed within the measurement chamber, e.g. the effective optical path through which a light is projected through a specimen fluid is highly dependent on the volume of specimen fluid introduced into the well.

Therefore, there is a need for apparatuses and methods which allow for large numbers of tests to be conducted quickly and efficiently without the need for tight control over specimen fluid volumes. Such apparatuses and methods will likely have the positive effects of reducing the overall cost of healthcare. Moreover, such apparatuses and methods may increase the amount of research and development that companies can dedicate to ailments of the world's more needy and less affluent populations by reducing the cost of testing and, resultantly, increasing the number of potential drugs which companies can justify financial investment in.

Accordingly, this application discloses apparatuses and methods which allow for a high degree of control over the optical path length of a specimen fluid whilst taking photometric measurements in the generally vertical orientation such as is desirable for performing many tests in a short time period, for example on a microplate comprising a plurality of sample wells.

SUMMARY

This section provides a general summary of the disclosure, and it is not a comprehensive disclosure of its full scope or all of its features.

An apparatus for taking an accurate photometric measurement of a liquid by way of forming a specimen volume of a controlled optical path length for use with photometric measurement equipment is disclosed herein. In some embodiments, the apparatus comprises a transparent body configured for displacing a volume of a fluid and at least one support element wherein the support element is configured to maintain the transparent body at a location such that specimen fluid may enter a void volume to form a specimen volume of a controlled optical path length. In some embodiments, the apparatus comprises a plurality of transparent bodies interconnected by a web such that the transparent bodies are maintained at a spacing arrangement which allows for them to be inserted into the wells of a microplate in order to create a plurality of specimen volumes of a controlled optical path length.

The following embodiments and descriptions are for illustrative purposes only and are not intended to limit the scope of the apparatus for taking an accurate photometric measurement of a liquid. Other aspects and advantages of the present invention will become apparent from the following detailed description.

BRIEF DESCRIPTION OF THE DRAWINGS

These and other features, aspects, and advantages of the present disclosure will become better understood with regard to the following description, appended claims, and accompanying drawings. The drawings described herein are for illustrative purposes only of selected embodiments and not all possible implementations and are not intended to limit the scope of the present disclosure.

The drawings included herein are considered by the applicant to be informal.

FIG. 3 and FIG. 4 show a perspective view and a front elevation view, respectively, of an apparatus in accordance with a second embodiment of the present disclosure.

FIGS. 5-9 show various views of an apparatus in accordance with a third embodiment of the present disclosure and, more particularly, to an embodiment intended to cover a specimen fluid within a petri dish.

FIGS. 17-26 show various views of an apparatus in accordance with a sixth embodiment of the present disclosure and, more particularly, to an embodiment intended to be inserted into a specimen receptacle, e.g. a cuvette, in order to create at least one generally horizontal controlled optical path length.

DETAILED DESCRIPTION

Figure 2:
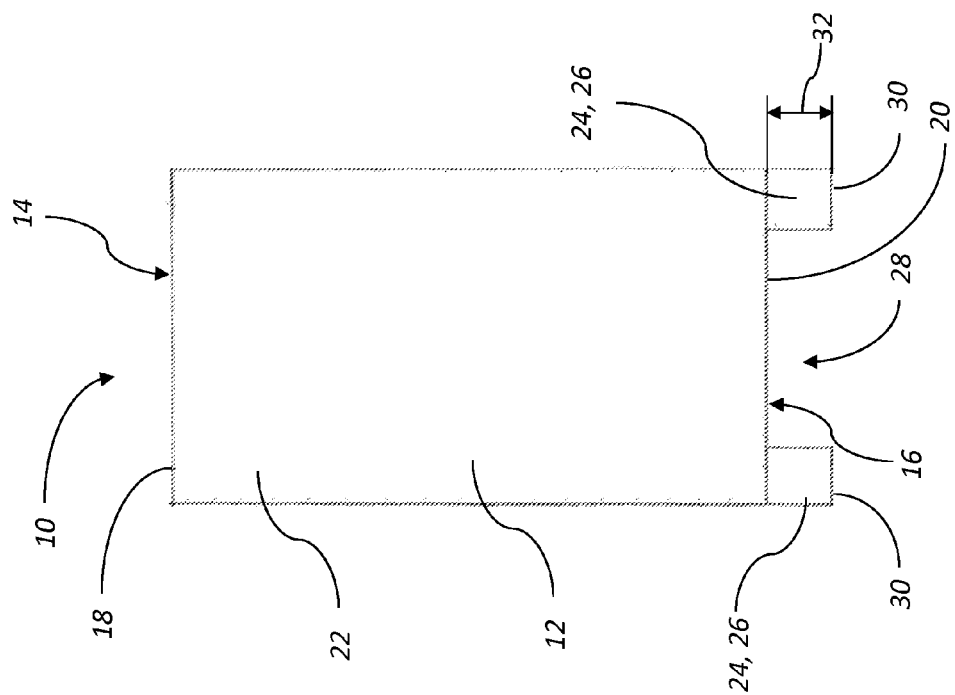
FIG. 1 and FIG. 2 show a perspective view and a front elevation cross-sectional view, respectively, of an apparatus for taking an accurate photometric measurement of a liquid by way of forming a specimen volume of a controlled optical path length for use with photometric measurement equipment in accordance with a first embodiment of the present disclosure.

Following is a description by way of example only and with reference to the accompanying informal drawings of a manner of constructing and using the apparatus for taking accurate photometric measurements of fluids. Example embodiments are provided to fully convey the scope of this disclosure to those skilled in the art. The present apparatus for taking an accurate photometric measurement of a liquid may have additional embodiments, may be practiced without one or more of the details described for any particular described embodiment, or may have any detail described for one particular embodiment practiced with any other detail described for another embodiment. Numerous specific details are set forth as examples and are intended to provide a thorough understanding of embodiments of the present disclosure. It will apparent to one skilled in the art that these specific details need not be employed, that example embodiments may be embodied in many different forms, and that neither should be construed to limit the scope of the disclosure. In some example embodiments, well-known processes, well-known device structures, and well-known technologies are not described in detail. Moreover, the method steps, processes, and operations described herein are not to be construed as necessarily requiring their performance in any particular order discussed or illustrated, unless specifically identified as an order of performance. It is also to be understood that additional or alternative steps may be employed.

The apparatus, according to some embodiments, is intended to be used in conjunction with existing laboratory equipment, e.g. standard cuvettes and microplates already widely used with spectrometers, by inserting the apparatus into one or more sample wells of a microplate or into the sample region or well of a cuvette. Inserting the apparatus into a sample well creates a void volume underneath a transparent body of the apparatus due to one or more support elements maintaining the position of various elements of the apparatus. Specifically, in a preferred embodiment the apparatus comprises a plurality of legs beneath the transparent body which maintains a bottom surface of the transparent body at a controlled height above a generally flat surface upon which the apparatus rests. Thus, the apparatus having been inserted into a sample well and a bottom surface of the transparent body being maintained at a controlled height above the floor of the sample well to create a void volume, a specimen fluid may now be introduced into the sample well to be displaced by the transparent body. The displacement by the transparent body of any fluid which otherwise would accumulate above the bottom surface of the transparent body, i.e. within the volume of space occupied by the volume of the transparent body, results in the formation of a specimen volume of a controlled optical path length for use with photometric measurement equipment.

Preferably, the upper boundary and the lower boundary of the specimen volume of a controlled optical path, as defined by the bottom surface of the transparent body and the floor of the sample well respectively, are generally parallel to each other and also perpendicular to the direction in which the light source from a spectrometer is to be projected.

Because some embodiments are intended to rest on the floor of a sample well whilst submerged in a fluid, the density of the apparatus must be sufficient to overcome the buoyancy effects of the specimen fluid. Many specimen fluids will be water based and, therefore, the density of the apparatus is preferably greater than the density of the specimen fluid such that the apparatus is negatively buoyant, i.e. it sinks in the specimen fluid.

The term specimen fluid is used in its broad sense of a substance having particles that easily move and change their relative position without a separation of the mass and that easily yield to pressure, i.e. a substance that is capable of flowing. Therefore, fluid is meant to encompass at least liquids and gases. For example, the apparatus is intended to function with a specimen fluid of atmospheric air or pure water in order to calibrate a photometric measurement device. For example, when measuring properties of a specimen fluid by spectrophotometry the fluid is place in a specimen holder, e.g. a cuvette or a sample well of a microplate, and then light of a particular wavelength is passed through the solution inside the specimen holder. The amount of light transmitted through and absorbed by the specimen fluid is measured. Although the measurement of concern is often the amount of light absorbed by a compound dissolved into the specimen fluid and the fact that the solution itself may absorb an amount of light, the transmittance and absorbance of a specimen fluid is typically compared to that of a reference blank. Preferably, the reference blank is identical, both geometrically and molecularly, to the specimen fluid as set up for testing with the sole exception that the substance being analyzed is omitted. Because the substance being tested is omitted in the reference blank, the transmittance of the reference blank is defined as 100% T. This number is multiplied by 100 to determine the percent transmittance (% T), the percentage of light transmitted by the substance relative to the reference blank. Thus, the percent transmittance through the substance being analyzed is defined as % $T=I/I_0 \times 100$.

As used herein, the term "transparent", as used to describe the transparent body, is not intended to require the body to transmit one hundred percent of light passing through the body. The term transparent is simply meant to denote that the body allows the passage of one or more specified forms of radiation, e.g. X-rays or ultraviolet light. Moreover, as used herein the term transparent body is not limited to bodies which are transparent to light propagating in all directions or against all outer surfaces of the transparent body. It is simply used to mean that merely at least a portion of the body is transparent. For example, a cubic body having a top and a bottom which are transparent, four side surfaces which are non-transparent, and a transparent inner volume as defined by the six surfaces falls under the intended meaning of transparent body. In some embodiments, one or more surfaces of the transparent body of the apparatus may comprise ridges or other surface features to either scatter light or aid in physical manipulation of the apparatus, e.g. by a user's hand.

The terms "generally," "substantially," or other terms of degree may be utilized herein to represent the inherent degree of uncertainty that may be attributed to any quantitative comparison, value, measurement, or other representation. One skilled in the art will recognize that in manufacturing any tangible apparatus there may be predetermined tolerance specifications defining the allowable variation from nominal dimensions. For example, a standard for microplate dimensioning numbered ANSI/SLAS 1-2004 published by the American National Standards Institute discloses the acceptable variance from true parallelism certain surfaces may have. The terms are also used herein to represent the degree by which a quantitative representation may vary from a stated reference without resulting in a change in the basic function of the apparatus for taking an accurate photometric measurement of a liquid.

The term "void volume" is intended to describe the geometrical features of the apparatus itself without limiting the intended use of the apparatus. It will be appreciated that even when the apparatus is not in use, the void volume will contain at least air and, moreover, that the void volume will contain a specimen during the normal intended use of this apparatus. Thus, the term "void volume" shall not be construed to require that the volume contain no matter whatever.

Figure 1:
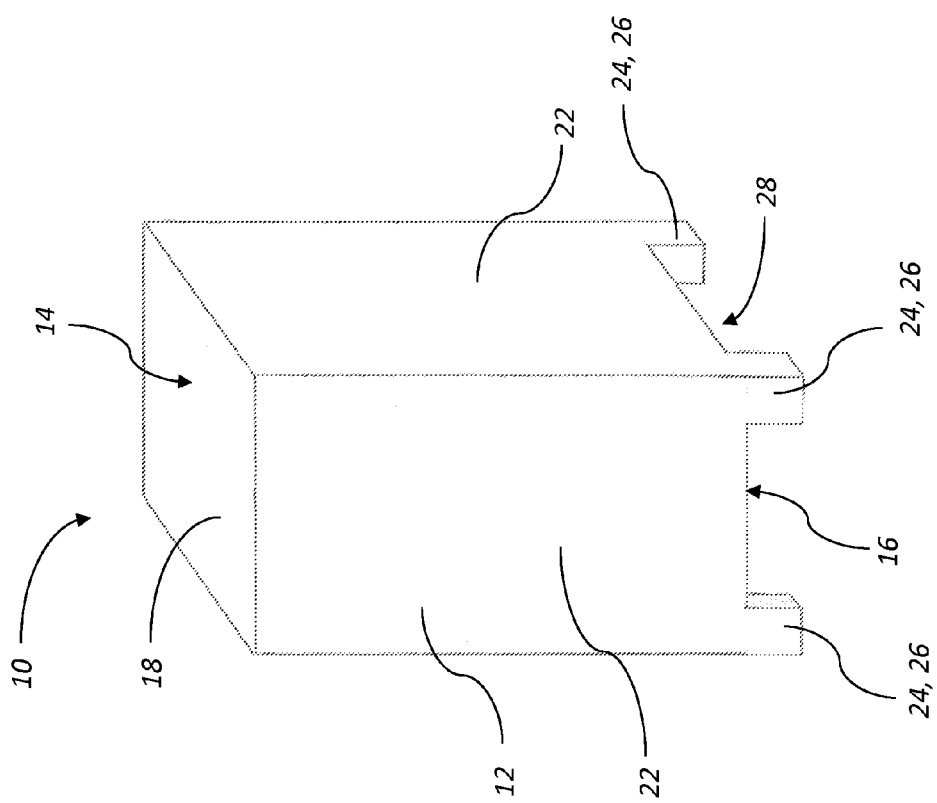

Referring now to the drawings, FIGS. 1-2 show a perspective view and a front elevation cross-sectional view, respectively, of an apparatus 10 for taking an accurate photometric measurement of a liquid in accordance with a first embodiment of the present disclosure. The apparatus 10 includes a transparent body 12 having a top end 14 and a bottom end 16. The transparent body 12 comprises six main surfaces including a top surface 18, a bottom surface 20, and four side walls 22. As previously stated, the transparent body 12 is preferably negatively buoyant such that it will sink into specimen fluids, e.g. fused quartz may be used due to its desirable transparent optical properties as well as its density of roughly 2.203 grams per cubic centimeter which is 2.203 times the density of water. The transparent body 12 may also be made of glass, plastic, ultraviolet quartz, or any another suitable material for use with the intended wavelength of light. The apparatus also includes at least one support element 24 and, typically, the support element(s) 24 extend outwardly from the bottom end 16. In the preferred embodiment illustrated in FIGS. 1-2, the support elements 24 comprise four legs 26 extending outwardly from the bottom surface 20. A void volume 28 is disposed within the region laying between the bottom surface 20 and an outermost part 30 of the support elements 24.

With particular reference to FIG. 2, the front elevation cross-sectional view shows the void volume 28 and, more particularly, that the height 32 of the void volume 28 is controlled by the distance of the outermost part of the support element 30 from the geometric plane defined by the bottom surface 20. When the apparatus 10 is submerged within a specimen fluid (not shown), e.g. within the sample region or well of a cuvette, a volume of specimen fluid is formed, within the void volume 28, having a controlled height 32 thereby ensuring a controlled optical path length for use with photometric measurement equipment. Using the apparatus to perform a typical measurement procedure may include placing the apparatus 10 within a cuvette (not shown) and then filling the cuvette with water to at least a level greater than the controlled height 32 to "blank" the equipment as described above. The user may then replace the water with a specimen fluid, e.g. a compound dissolved in water, and then measure the transmittance and absorbance of the specimen fluid. Because the optical path length is accurately defined by the controlled height 32 rather than loosely defined by a difficult to control fill level as would be necessary without the apparatus 10, significant error is eliminated from the calculations based on the photometric measurements.

Referring now FIGS. 3-4, a perspective view and a front elevation cross-sectional view, respectively, are shown of an apparatus 40 for taking an accurate photometric measurement of a liquid in accordance with a second embodiment of the present disclosure. The apparatus 40 includes a transparent body 42 having a top end 44 and a bottom end 46. In this embodiment, the transparent body 42 is generally cylindrical in shape such that it comprises a single side wall 48. Preferably, the diameter of the transparent body 42 is slightly less than the diameter of a chosen microplate sample well such that the apparatus 40 is easily insertable into a microplate well. The top end 44 comprises a top surface 50 and the bottom end 46 comprises a bottom surface 52 wherein the top surface and the bottom surface are generally planar and parallel to each other. Similar to the first embodiment disclosed herein, this embodiment also includes at least one support element 54 and, typically, the support element(s) 54 extend outwardly from the bottom end 46. Preferably, the support elements 54 comprise three legs 56 extending outwardly from the bottom surface 52 to form a void volume 58 disposed within the region laying between the bottom surface 50 and an outermost part 60 of the support elements 54.

With particular reference to FIG. 4, the front elevation cross-sectional view shows the void volume 58 and, more particularly, that the height 62 of the void volume 58 is controlled by the distance of the outermost part of the support element 60 from the geometric plane defined by the bottom surface 52. This embodiment functions similarly to the first embodiment in that it is intended to be partially submerged within a specimen fluid (not shown), to form a specimen volume of a controlled height thereby creating a tightly controlled optical path length. It will be immediately recognized by one of ordinary skill that the optical path length, e.g. the distance that light travels through a specimen fluid prior to being measured once it exits the fluid, is defined by the height 62 of the bottom surface 52 above whatever surface the apparatus rests upon which, during its intended use, is most likely the inner floor of a cuvette or microplate well.

Still referring to FIGS. 3-4, the apparatus 40 further comprises a channel 64 running through the transparent body with openings at both the top end 44 and the bottom end 46 to allow for the passage of fluids past the transparent body 42 and into the void volume 58 underneath the bottom surface 52. One of ordinary skill will recognize that the apparatus 40 will serve its intended function when the specimen fluid is added in an amount to create a fill level laying at a level within the channel 64, i.e. between the bottom surface 52 and the top surface 50.

In some embodiments, the apparatus further comprises a tab (not shown) extending upwardly from the top end in order to facilitate easy manipulation, e.g. insertion and extraction into and out of a sample well. In some embodiments, the apparatus comprises a plurality of surfaces configured at different heights to create a plurality of optical path lengths. For example, the apparatus may comprise a series of stepped surfaces with the lowest of the stepped surfaces being the bottom surface, wherein each of the individual surfaces is set at a different height above the outermost part of the support elements such that a plurality of tests may be conducted bases on a plurality of different optical path lengths without a need to change the experiment equipment set up between tests. Such features may be practice with any embodiment of the apparatus whether or not the specific embodiment is disclosed herein.

FIGS. 5-9 show various views of an apparatus in accordance with a third embodiment of the present disclosure and, more particularly, to an embodiment intended to cover a specimen fluid within a petri dish. In this embodiment, the apparatus 70 comprises a transparent body 72 comprising a top surface 74 and a bottom surface 76. The apparatus 70 further comprises at least one side wall 78 for displacing specimen fluid. A specimen cover 80 extends outwardly from the side wall 78 and an outer wall 82 extends downward from the specimen cover 80. The outer wall 82 comprises an outer surface 84 and an inner surface 86 wherein the inner surface is configured to loosely mate with a predetermined specimen receptacle. For example, in the illustrated embodiment the apparatus 70 is intended for use with a petri dish (shown in dashed lines in FIGS. 5, 7, and 8) and, accordingly, the inner surface 86 diameter is sized to mate with said petri dish size.

With particular reference to FIGS. 7-8, the apparatus 70 may comprise a plurality of support elements, and in the illustrated embodiment the plurality of support elements comprises a plurality of legs 88. Also shown, in FIGS. 5, 7, and 8, is a petri dish 94 in in dashed lines because it is an environmental aspect which the apparatus 70 is intended to be used with. With particular reference to FIG. 7, a test specimen fill level 71 is shown at a level slightly above the bottom surface 76 of the apparatus 70 thereby displacing any fluid which would otherwise come to rest at a level above the bottom surface 76 if the apparatus 70 were removed. With particular reference to FIGS. 7-8, these cross-section views show that in this embodiment a plurality of legs 88 extend downwardly from the bottom surface 76 to define a void volume 90 of a controlled height 92 in order to tightly control an optical path length of a specimen fluid. Also shown in FIGS. 5-9 is that this embodiment comprises a shelled out volume between the at least one side wall 78 and above the transparent body 72. Shelled out is intended to mean that the volume between the at least one side wall 78 and above the transparent body 72 and below the plane defined by the specimen cover 80 is, in this embodiment, not solid material but rather simply an outline of the geometry needed to displace a fluid. Therefore, light is required to travel a minimum distance through the apparatus material and the amount of light absorbed by the apparatus 70 is minimized.

This third embodiment has the specific benefit that a test specimen, e.g. a growing cell culture, can be examined or tested in the original container, i.e. the petri dish which the cell culture is actually growing in. Thus, no transferring of the test specimen from its original container into a test specimen is needed by pipette or otherwise. This is beneficial because each transfer of the test specimen opens the specimen up to the vulnerability of contamination. Also, the controlled height 92 can be chosen based on the absorbance of the test specimen fluid and can be changed as the absorbance increases, e.g. as a cell culture grows over time the cell density increases and the specimen becomes more absorbent. Other benefits will be apparent to one skilled in the art based on their specific uses of laboratory equipment.

Figure 11:
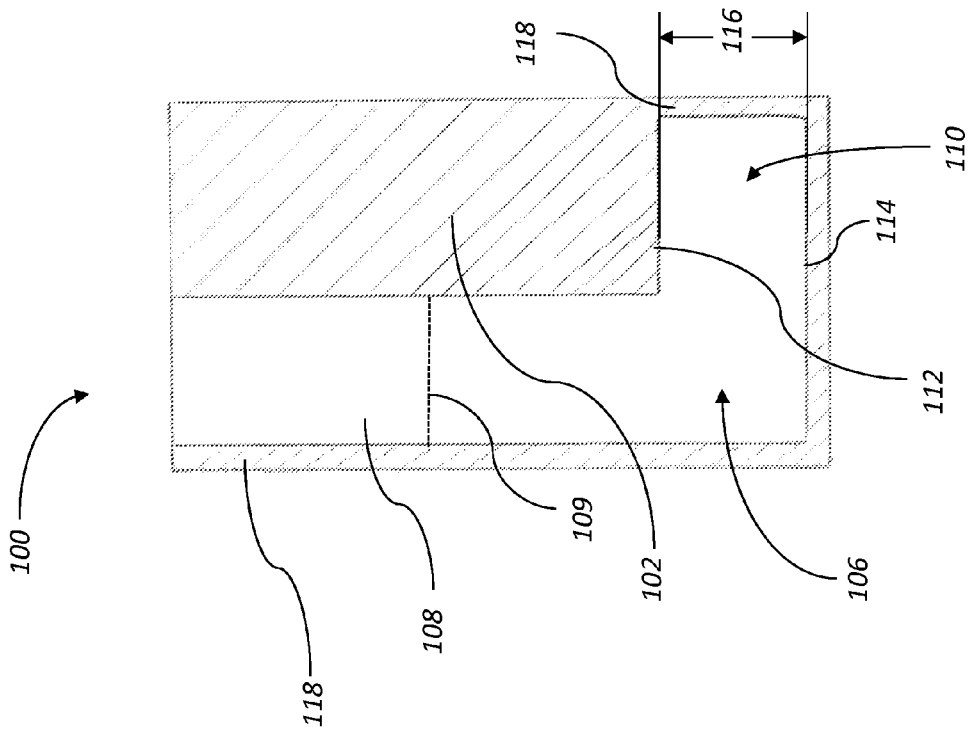
FIGS. 10-11 show a perspective view and a front elevation cross-sectional view, respectively, of an apparatus in accordance with a fourth embodiment of the present disclosure.
Figure 10:
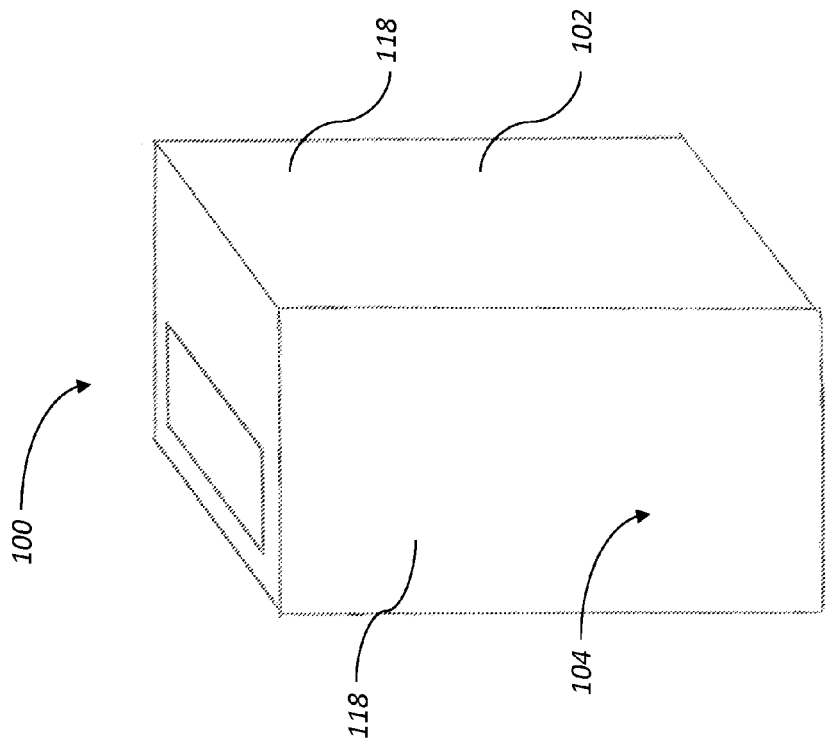

Referring now to FIGS. 10-11, a perspective view and a front elevation cross-sectional view, respectively, of an apparatus 100 in accordance with a fourth embodiment of the present disclosure shows that the transparent body 102 of this embodiment is integrated into a specimen receptacle 104. For example, in some embodiments the transparent body is integrated into a cuvette. In such embodiments, the specimen receptacle 104 comprises an inner region 106 for containing a specimen and a channel 108 through which a specimen may pass through to enter the inner region including a void volume 110 within the inner region. The void volume 110 is defined, in part, by the bottom surface 112 of the transparent body 102 and the floor 114 of the specimen receptacle 104 and, as in other embodiments, the height 116 of the void volume defines a tightly controlled optical path length. In addition to the floor 114, the apparatus 100 comprises four walls 118 which form the inner region 106. In the illustrated embodiment, three out of the four walls 118 comprise support the transparent body 102. Also, shown is a test specimen fluid fill level 109 which is above the bottom surface 112 such that the transparent body displaces fluid to control the optical path length as defined by the height 116.

Referring now to FIGS. 12-16, a various views of an apparatus 120 are shown in accordance with a fifth embodiment of the present disclosure. This embodiment is similar to the second embodiment with a key difference that there are a plurality of transparent bodies 122 interconnected by a web element 124 to maintain the transparent bodies 122 at a predetermined space from each other based on the spacing of the wells of a microplate such that the plurality of transparent bodies 122 may be inserted into a plurality of wells. The web element 124 interconnects all ninety-six transparent bodies in the illustrated embodiment. In some embodiments, the web element 124 is a sprue from an injection molding process which is simply left in place after the material passes through the sprue in the die. In injection molding, the term sprue refers to the passages through which a liquid material (such as polystyrene or polyvinyl chloride) flows into a die, where it solidifies to form parts. It also refers to the material which solidifies in these passages, forming a framework attaching the parts together in a roughly planar arrangement.

Figure 16:
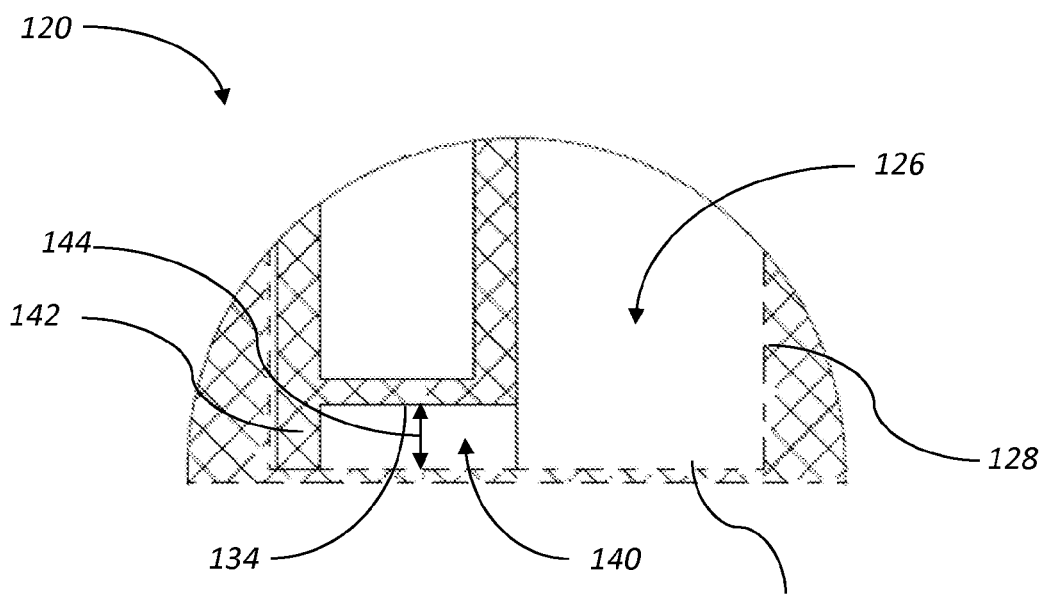

For clarity the views do not include a microplate with the exception of FIG. 16 which shows a generally cylindrical microplate well 126 having a side wall 128 and a floor 130. In this embodiment, each transparent body 122 comprises a top surface 132 and a bottom surface 134. Optionally, transparent bodies 122 further comprise a hollow inner region 136.

Figure 12:
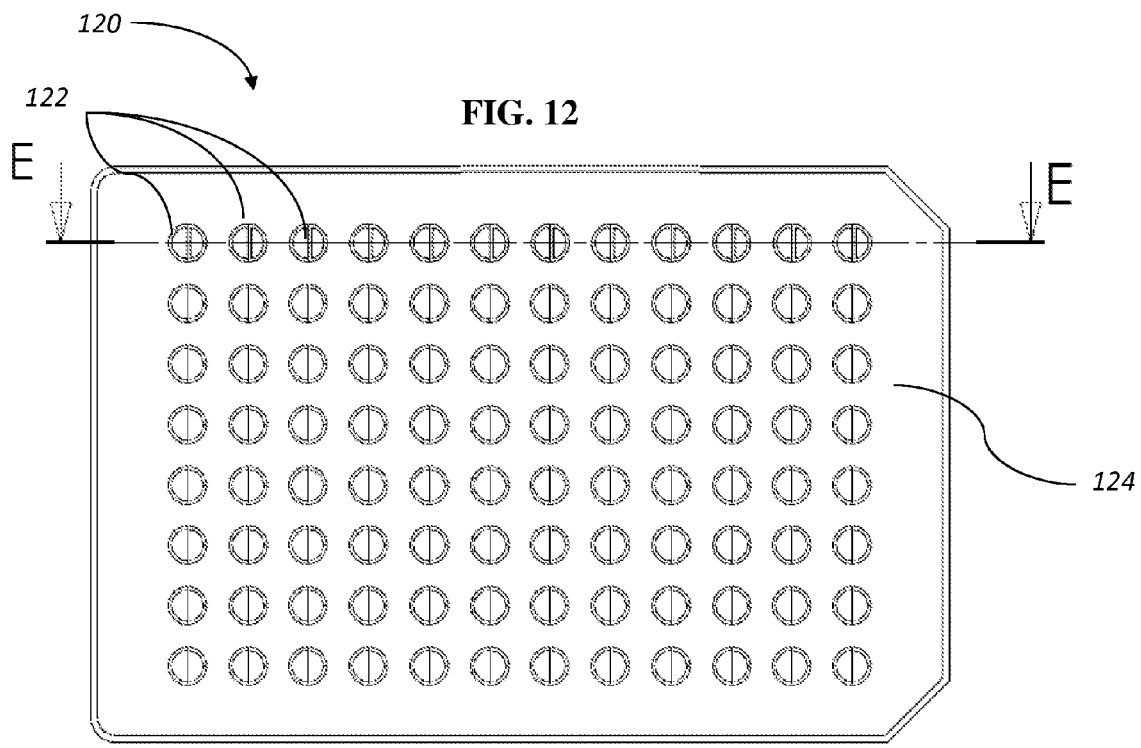
FIGS. 12-16 show various views of an apparatus in accordance with a fifth embodiment of the present disclosure and, more particularly, to an embodiment intended to cover a microplate and create controlled optical path lengths of a test specimen within plurality of wells within the microplate.

With particular reference to FIG. 12, a top view of the apparatus 120 is shown in order to illustrate the spacing of the plurality of transparent bodies. For clarity, i.e. to keep the drawings from being too busy, only the top left three transparent bodies 122 are labeled in the drawing. Also shown is a plurality of openings 138 (labeled in FIG. 15 only) in the web element 124 to allow for a specimen fluid to pass through into the microplate well and, more specifically, into a void volume 140 created underneath the bottom surface 134 of one or more of the plurality of transparent bodies.

Figure 13:
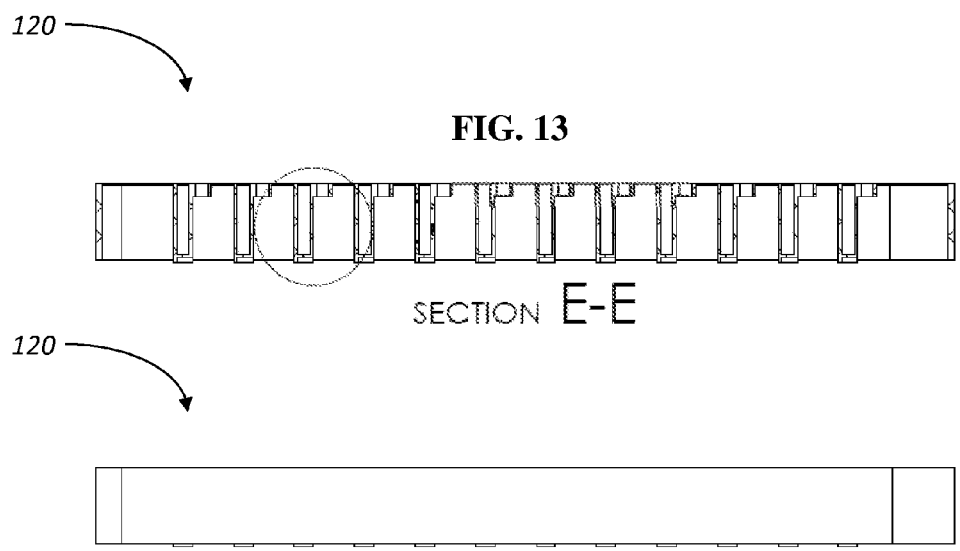
Figure 14:
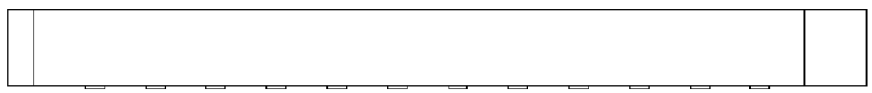
Figure 15:
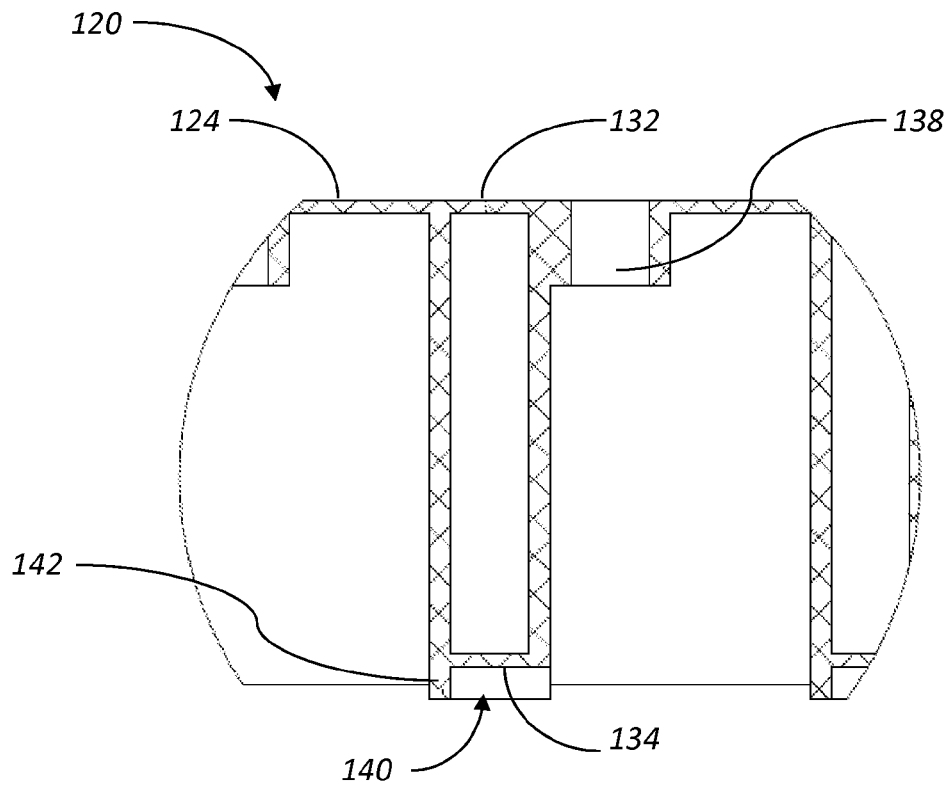

FIG. 13 illustrates cross-section view of FIG. 12 taken along line E-E and FIG. 15 illustrates the enlarged section view of the circle of FIG. 13. With particular reference to FIG. 15 the apparatus further comprises at least one support element 142 and, in the illustrated embodiment, this support element extends downwardly from the bottom surface 134 of one or more of the plurality of transparent bodies 122. This embodiment is described for illustrative purposes only and is not intended to limit the available ways in which the at least one support element 142 can maintain the bottom surface 134 of the transparent bodies 122 at a controlled height 144 (see FIG. 16) above the floor 130 of the microplate wells.

Referring now to FIGS. 17-26, various views of an apparatus 150 are shown in accordance with a sixth embodiment of the present disclosure. This embodiment is intended to be inserted into a specimen receptacle, e.g. a cuvette, which already has a volume of fluid within it in order to displace a volume of fluid to create at least one generally horizontal optical path length 153 as shown in FIG. 22. The sum of the at least one optical path lengths forms a controlled total optical path length. The benefits of such an embodiment include: that it can be used in a traditional spectrometer which directs light horizontally through a cuvette and measures the light properties on the opposite side as the light source; it enables even a small volume of fluid to be enough for testing which is desirable as many test specimens are expensive; it is easy to clean; no transferring of the test specimen is needed; and the height of the test specimen within the cuvette is always visible.

Referring now particularly to FIGS. 17-20, the apparatus 150 comprises a transparent body 151 having a first surface 152 and a second surface 154 which are generally planar, generally parallel, and are set at a distance from each other such that the apparatus is configured for insertion into a specimen receptacle to create at least one optical path length. For example, if the inner walls of a standard cuvette are spaced at a distance of 10 millimeters (mm) from one another then the first surface 152 and the second surface 154 may be set at a distance of 9 mm from one another in order to create a controlled total optical path length of 1 mm upon insertion of the apparatus into the cuvette. The apparatus also comprises at least one support element 156 and, in the illustrated embodiment, the at least one support element 156 is configured to support the apparatus from the top surface of a cuvette. Referring particularly to FIG. 17 a front view of the apparatus 150 is shown and best illustrates the support element 156 of this embodiment. Moreover, FIG. 23 illustrates the at least one support element resting on the top surface of a cuvette. Referring particularly to FIG. 18 a side view of the apparatus is shown which illustrates the first surface 152 and the second surface 154. Moreover, in the illustrate embodiment the transparent body extends upwardly to the support element whereas in some embodiments the transparent body 151 is maintained in a location by some other structural member such as, for example, a wire extending from the support element 156. Referring to FIGS. 21-26, the apparatus is shown in various views inserted into a cuvette 158.

While preferred and alternate embodiments have been illustrated and described, as noted above, many changes can be made without departing from the spirit and scope of the apparatus for taking an accurate photometric measurement of a liquid. Accordingly, the scope of the apparatus for taking an accurate photometric measurement of a liquid is not limited by the disclosure of these preferred and alternate embodiments. Instead, the scope of the apparatus for taking an accurate photometric measurement of a liquid should be determined entirely by reference to the claims.

Insofar as the description above and the accompanying drawing disclose any additional subject matter that is not within the scope of the claim(s) below, the inventions are not dedicated to the public and the right to file one or more applications to claim such additional inventions is reserved.

What is claimed is:

1. An apparatus for taking accurate photometric measurements of fluids, comprising:
   a transparent body having a top end and a bottom end, wherein
      the top end comprises a top surface, and
      the bottom end comprises a bottom surface;
   at least one side wall;
   at least one support element; and
   a void volume disposed between the bottom surface of the transparent body and at least one outermost part of the at least one support element; wherein
      the transparent body is configured for displacing a volume of a fluid, and
      the at least one support element is configured to maintain the bottom surface of the transparent body at a predetermined distance from a surface upon which the at least one support element may rest such that a volume of fluid may enter the void volume to form a specimen volume of a controlled optical path length.

2. The apparatus of claim 1, further comprising a specimen cover extending outwardly from the at least one side wall.

3. The apparatus of claim 2, further comprising an outer wall extending generally downwardly from the specimen cover, the outer wall having at least one inner surface and at least one outer surface.

4. The apparatus of claim 1, further comprising a specimen receptacle, the specimen receptacle comprising:
   an inner region for containing a specimen; and
   a channel through which a specimen may pass through to enter the inner region for containing a specimen, wherein
      the transparent body is positioned at least partially within the inner region of the specimen receptacle,
      the void volume is disposed within the inner region such that a specimen may pass through the channel to enter the void volume.

5. The apparatus of claim 4, wherein at least a portion of the specimen receptacle comprises the at least one support element.

6. The apparatus of claim 1, wherein the at least one support element extends generally downwardly from the bottom end of the transparent body.

7. The apparatus of claim 1, wherein the bottom surface of the transparent body and the top surface of the transparent body are each generally planar and are generally parallel to each other.

8. The apparatus of claim 1, wherein at least a portion of the at least one side wall is non-transparent.

9. The apparatus of claim 1, wherein the transparent body comprises at least one of glass, plastic, quartz, or any combination thereof.

* * * * *